United States Patent
Eaton

(10) Patent No.: US 8,348,987 B2
(45) Date of Patent: Jan. 8, 2013

(54) BALLOON WITH SCORING MEMBER

(75) Inventor: Elizabeth A. Eaton, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 220 days.

(21) Appl. No.: 12/645,122

(22) Filed: Dec. 22, 2009

(65) Prior Publication Data
US 2011/0152905 A1    Jun. 23, 2011

(51) Int. Cl.
*A61F 2/06* (2006.01)
*A61B 17/22* (2006.01)

(52) U.S. Cl. .................. 623/1.11; 606/159

(58) Field of Classification Search ............ 606/194, 606/192, 191, 198, 195, 108, 159, 167, 170, 606/127, 128; 623/1.15, 1.16, 1.22, 1.11, 623/1.18, 1.2, 1.12, 1.14, 1.3, 1.19; 604/509, 604/920, 22, 915, 916, 96.01, 103.05–103.08, 604/99.01, 97.01, 97.02, 103.11, 103, 913; 428/36.9

See application file for complete search history.

(56) References Cited

U.S. PATENT DOCUMENTS

| | | | |
|---|---|---|---|
| 4,729,763 A | 3/1988 | Henrie | |
| 4,886,061 A | 12/1989 | Fischell et al. | |
| 4,898,575 A | 2/1990 | Fischell et al. | |
| 4,983,167 A | 1/1991 | Sahota | |
| 5,019,042 A | 5/1991 | Sahota | |
| 5,030,201 A | 7/1991 | Palestrant | |
| 5,047,040 A | 9/1991 | Simpson et al. | |
| 5,057,120 A | 10/1991 | Farcot | |
| 5,078,723 A | 1/1992 | Dance et al. | |
| 5,080,660 A | 1/1992 | Buelna | |
| 5,090,958 A | 2/1992 | Sahota | |
| 5,112,305 A | 5/1992 | Barath et al. | |
| 5,147,377 A | 9/1992 | Sahota | |
| 5,160,321 A | 11/1992 | Sahota | |

(Continued)

FOREIGN PATENT DOCUMENTS

EP    117519 A1    9/1984

(Continued)

OTHER PUBLICATIONS

AngioScore, Inc., ©2004-2009, AngioScore®, AngioSculpt®PTCA, "A New Dimension in Patient Outcomes," [online][retrieved from internet: URL http://www.angioscore.com/coronary-product/], [retrieved on May 20, 2009], 5 pages.

*Primary Examiner* — Victor Nguyen
*Assistant Examiner* — Jocelin Tanner
(74) *Attorney, Agent, or Firm* — Brinks Hofer Gilson & Lione

(57) ABSTRACT

A circumferentially and longitudinally continuous scoring structure having a diameter in an initial unrestrained state that is smaller than a deflated diameter of the balloon is disposed around an outer surface of the balloon in an expanded configuration. The scoring structure continually exerts a radially inward compressive force against the balloon such that when the balloon is expanded from a deflated configuration to an inflated configuration, the scoring structure expands in a radially outward direction and remains in continuous compressive contact with at least a portion of the balloon as the balloon unfolds. The scoring structure may be entirely free of attachment to the balloon and catheter, and may extend substantially a length of a working region of the balloon. The scoring structure may include a plurality of circumferentially compressible members connecting longitudinal members.

17 Claims, 15 Drawing Sheets

U.S. PATENT DOCUMENTS

| | | |
|---|---|---|
| 5,181,920 A | 1/1993 | Mueller et al. |
| 5,192,291 A | 3/1993 | Pannek, Jr. |
| 5,196,024 A | 3/1993 | Barath |
| 5,209,749 A | 5/1993 | Buelna |
| 5,224,945 A | 7/1993 | Pannek, Jr. |
| 5,224,949 A | 7/1993 | Gomringer et al. |
| 5,314,472 A | 5/1994 | Fontaine |
| 5,320,605 A | 6/1994 | Sahota |
| 5,320,634 A | 6/1994 | Vigil et al. |
| 5,336,178 A | 8/1994 | Kaplan et al. |
| 5,372,601 A | 12/1994 | Lary |
| 5,395,332 A | 3/1995 | Ressemann et al. |
| 5,409,454 A | 4/1995 | Fischell et al. |
| 5,411,478 A | 5/1995 | Stillabower |
| 5,431,673 A | 7/1995 | Summers et al. |
| 5,441,510 A | 8/1995 | Simpson et al. |
| 5,505,725 A | 4/1996 | Samson |
| 5,556,408 A | 9/1996 | Farhat |
| 5,571,087 A | 11/1996 | Ressemann et al. |
| 5,575,771 A | 11/1996 | Walinsky |
| 5,601,582 A | 2/1997 | Shelton et al. |
| 5,616,149 A | 4/1997 | Barath |
| 5,628,746 A | 5/1997 | Clayman |
| 5,690,642 A | 11/1997 | Osborne et al. |
| 5,728,129 A | 3/1998 | Summers |
| 5,779,698 A | 7/1998 | Clayman et al. |
| 5,792,158 A | 8/1998 | Lary |
| 5,797,935 A | 8/1998 | Barath |
| 5,814,061 A | 9/1998 | Osborne et al. |
| 5,843,027 A * | 12/1998 | Stone et al. .................. 604/509 |
| 5,904,679 A | 5/1999 | Clayman |
| 5,910,144 A | 6/1999 | Hayashi |
| 5,921,958 A | 7/1999 | Ressemann et al. |
| 6,033,380 A | 3/2000 | Butaric et al. |
| 6,036,689 A | 3/2000 | Tu et al. |
| 6,036,708 A | 3/2000 | Sciver |
| 6,071,285 A | 6/2000 | Lashinski et al. |
| 6,123,718 A | 9/2000 | Tu et al. |
| 6,165,187 A | 12/2000 | Reger |
| 6,231,572 B1 | 5/2001 | Hart et al. |
| 6,231,581 B1 * | 5/2001 | Shank et al. .................. 606/157 |
| 6,245,040 B1 | 6/2001 | Inderbitzen et al. |
| 6,264,690 B1 * | 7/2001 | Von Oepen .................. 623/1.3 |
| 6,280,464 B1 | 8/2001 | Hayashi |
| 6,283,947 B1 | 9/2001 | Mirzaee |
| 6,306,151 B1 | 10/2001 | Lary |
| 6,355,013 B1 | 3/2002 | van Muiden |
| 6,371,961 B1 | 4/2002 | Osborne et al. |
| 6,500,186 B2 | 12/2002 | Lafontaine et al. |
| 6,632,231 B2 | 10/2003 | Radisch, Jr. |
| 6,746,463 B1 | 6/2004 | Schwartz |
| 6,808,531 B2 | 10/2004 | Lafontaine et al. |
| 6,855,124 B1 | 2/2005 | Gonzalez et al. |
| 7,056,323 B2 * | 6/2006 | Mareiro et al. .................. 606/108 |
| 2002/0161388 A1 * | 10/2002 | Samuels et al. ............... 606/192 |
| 2003/0028212 A1 | 2/2003 | Saab |
| 2003/0114877 A1 | 6/2003 | Gellman |
| 2004/0122465 A1 | 6/2004 | McMurtry et al. |
| 2004/0143287 A1 | 7/2004 | Konstantino et al. |
| 2004/0193196 A1 | 9/2004 | Appling et al. |
| 2004/0199191 A1 | 10/2004 | Schwartz |
| 2005/0021070 A1 | 1/2005 | Feld et al. |
| 2005/0021071 A1 | 1/2005 | Konstantino et al. |
| 2005/0288629 A1 | 12/2005 | Kunis |
| 2006/0111736 A1 | 5/2006 | Kelley |
| 2006/0173487 A1 | 8/2006 | Uflacker et al. |
| 2006/0259005 A1 * | 11/2006 | Konstantino et al. ......... 604/500 |
| 2007/0073329 A1 | 3/2007 | Hardert |
| 2007/0106215 A1 | 5/2007 | Olsen et al. |
| 2007/0179598 A1 * | 8/2007 | Duerig ........................ 623/1.44 |
| 2007/0208416 A1 * | 9/2007 | Burpee et al. ................ 623/1.22 |
| 2007/0239262 A1 * | 10/2007 | Kula ............................ 623/1.16 |

FOREIGN PATENT DOCUMENTS

| | | | |
|---|---|---|---|
| WO | WO 2004/066852 A2 | 8/2004 | |

* cited by examiner

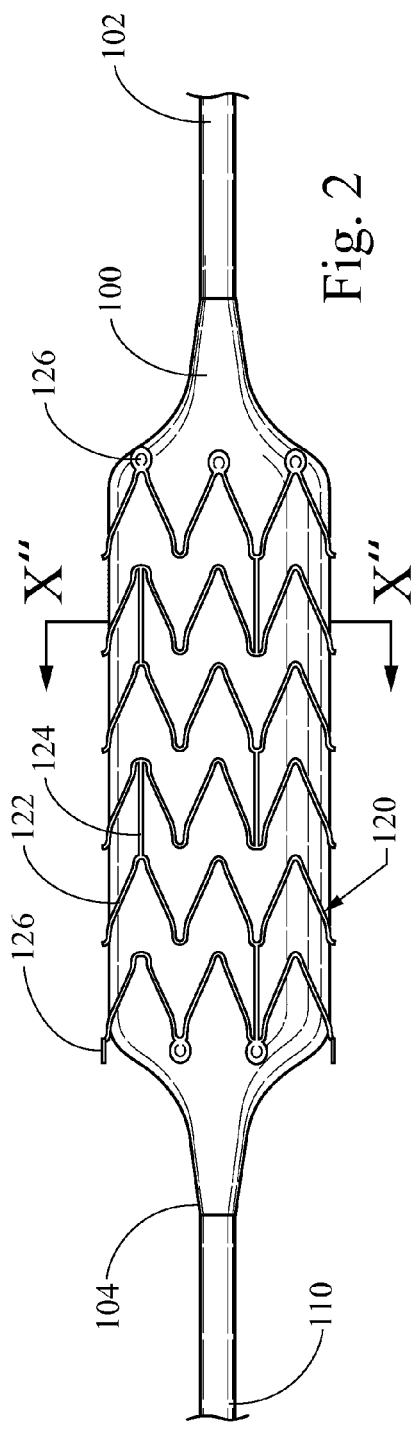
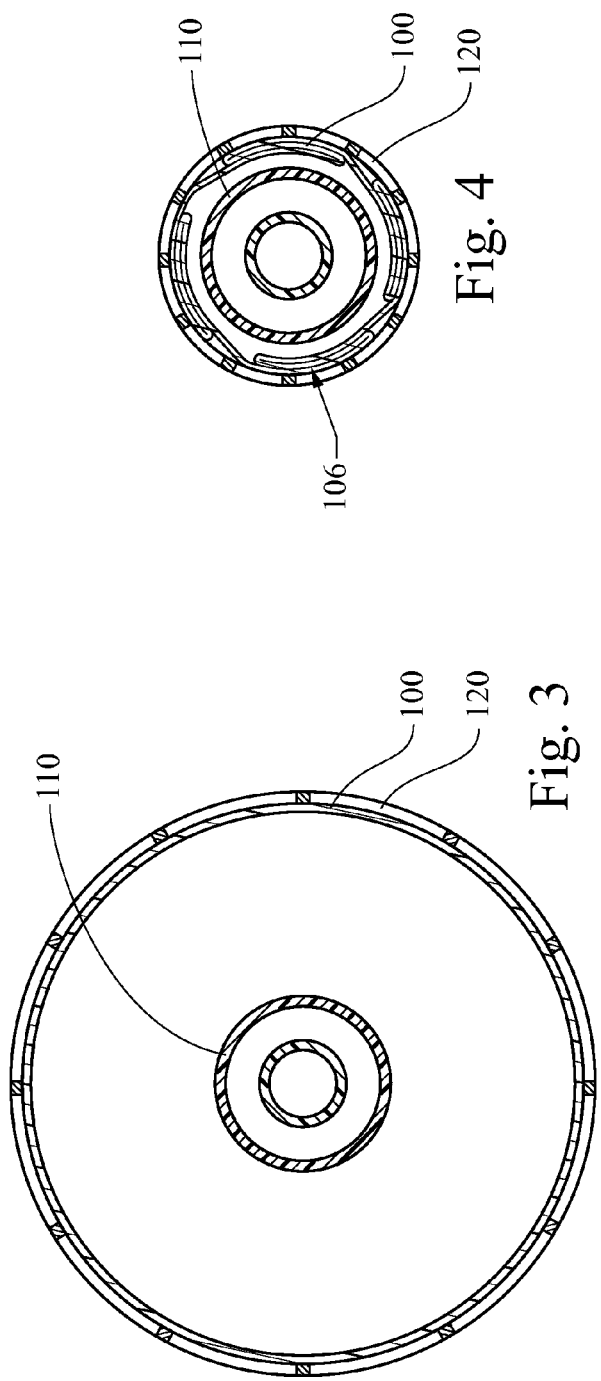

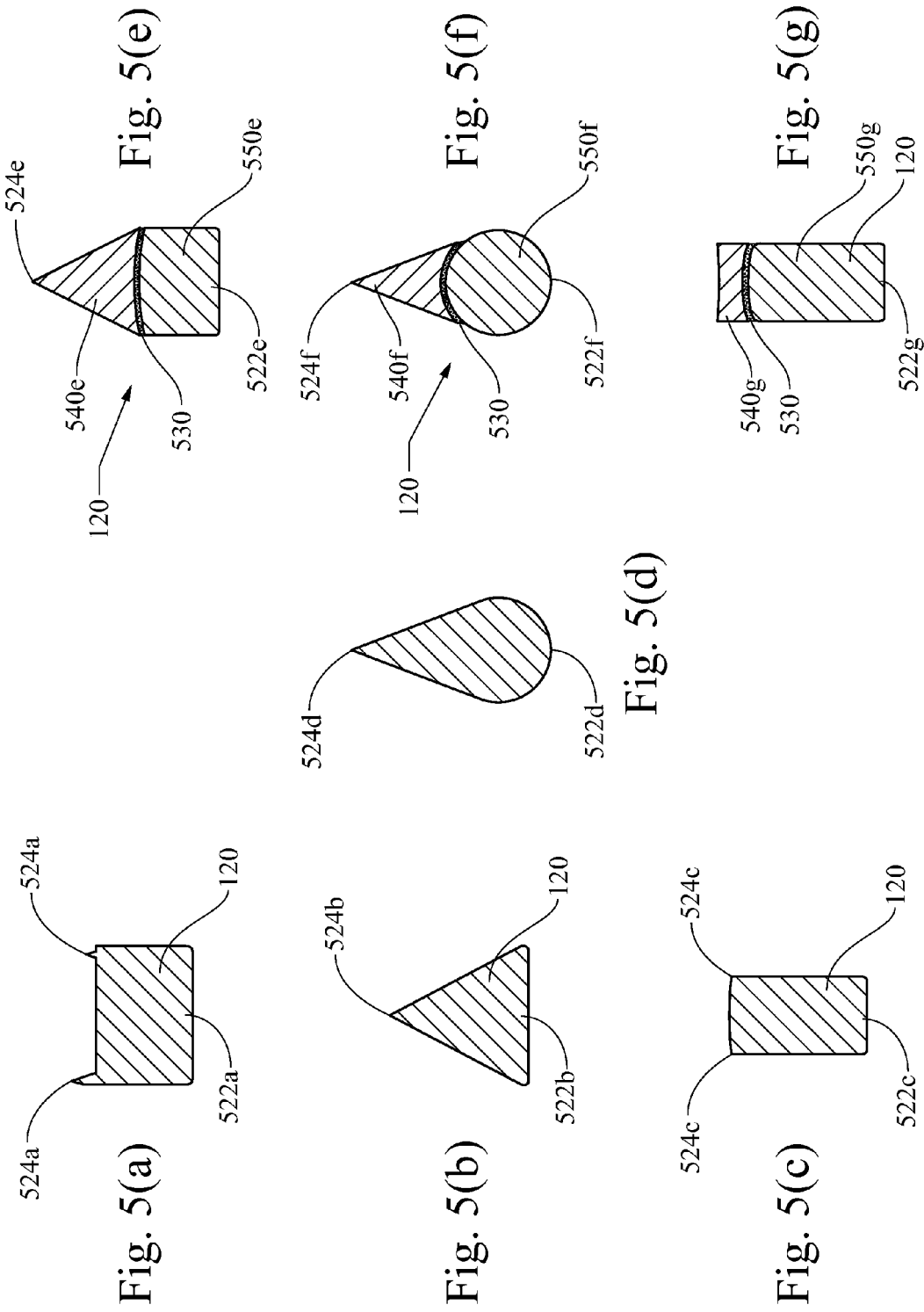

BALLOON WITH SCORING MEMBER

BACKGROUND

The present invention relates generally to medical devices and more particularly to balloon catheters.

Various medical conditions may affect patients in a variety of bodily passageways, such as vessels and ducts. One common condition is atherosclerosis, which begins with the accumulation of excess fats and cholesterol in a blood vessel. Atherosclerotic plaque forms within the walls of the vessel and may block or restrict blood flow through the vessel. This narrowed portion of the arterial lumen is commonly referred to as a stricture or stenosis. Generally, the coronary arteries, the aorta, the iliofemoral arteries and the carotid arteries are most commonly affected by stenosis. Several serious consequences may result from the restricted blood flow, such as ischemic events and blood clots that may block the artery.

There are various types of athlerosclerotic plaque that may form within the vessel wall. For example, some plaque may impede flow and exhibit a calcified or fibrous nature, while other plaque may be considered "vulnerable plaque." While vulnerable plaque may develop within the arterial walls without generally narrowing the arterial lumen substantially, occlusive lesions may include calcified or fibrous plaque comprising, for example, necrotic tissue. The necrotic tissue associated with fibrous plaque may cause the arterial wall to progressively weaken, and a rupture of the intima can occur, thereby causing aneurysm and hemorrhage.

Various procedures are known for treating such occlusions in the arterial vasculature, including balloon angioplasty and stenting. Although balloon catheters are used in many procedures other than angioplasty, coronary angioplasty using a balloon catheter has drawn particular attention from the medical community because of the growing number of people suffering from heart problems associated with stenosis. This has lead to an increased demand for medical procedures to treat such problems. The increased frequency of heart problems in recent years may be due to a number of societal changes, including, but not limited to insufficient exercise, obesity, and unhealthy diets in conjunction with an increase in the average life span as compared to previous generations.

Angioplasty procedures have become a popular alternative for treating coronary stenosis because angioplasty procedures are considerably less invasive than other alternatives. For example, stenosis of the coronary arteries has traditionally been treated with bypass surgery. In general, coronary bypass surgery is a very invasive procedure that is risky and requires a long recovery time for the patient. Typically, bypass surgery involves splitting the chest bone to open the chest cavity and grafting a replacement vessel onto the heart to bypass the blocked, or stenosed, artery.

During a balloon angioplasty procedure, a catheter having a deflated balloon attached thereto is inserted into a patient's vessel. During this stage, the balloon is uninflated and collapsed onto the catheter in order to present a low profile which may be passed through vessel lumens. Once positioned across a constricting lesion, the balloon is inflated by pumping a saline solution or a mixture of saline and contrast solution through the catheter to the balloon. As the balloon inflates, it is forced against the vessel wall and expands radially outward to widen the lumen to partially or fully restore patency to the vessel. This outward expansion of the vessel is typically referred to as dilation.

In the event a stent is mounted on the balloon, the balloon inflation may also serve to expand the stent and implant it within the artery. After satisfactory widening of the stenosis has been achieved, the balloon is deflated so that it once again collapses onto the delivery system. The catheter then is retracted and removed from the patient's vessel with the balloon in the deflated state. The balloon catheter is then retracted from the body. If a stent is mounted on the balloon of the catheter, the stent is left permanently implanted in its expanded state at the desired location in the vessel to provide a support structure that prevents the vessel from collapsing back to its pre-dilated condition. On the other hand, if the balloon catheter is not adapted for delivery of a stent, either a balloon-expandable stent or a self-expandable stent may be implanted in the dilated region in a follow-up or follow-on procedure.

It is not uncommon for stenosed regions to be formed of calcified or fibrous plaque comprising, for example, necrotic tissue. These types of stenosis can be difficult to completely dilate using conventional balloons because they tend to remain intact and resist expansion pressures applied by conventional balloon catheters.

SUMMARY

Angioplasty balloon catheters are described that may include any of the following aspects in various combinations and may also include any other aspect described below in the written description or in the attached drawings.

In one aspect, an angioplasty balloon catheter may include a balloon having a distal portion, and a proximal portion, and an active portion disposed therebetween. The active portion may have a working diameter sized to dilate a vessel wall. The balloon may be mounted on a distal end of a catheter, the catheter including an inflation lumen in fluid communication with an interior region of the balloon. The balloon is expandable between a deflated configuration having a first diameter in which the balloon is folded, and an inflated configuration having a second diameter in which the balloon is unfolded. The second, inflated diameter is greater than the first, deflated diameter.

The balloon catheter further includes a circumferentially and longitudinally continuous scoring structure having a diameter in an initial unrestrained state that is smaller than the first diameter of the balloon. The scoring structure is disposed around an outer surface of the balloon in an expanded configuration, the scoring structure thereby continually exerting a radially inward compressive force against the balloon such that when the balloon is expanded from the deflated configuration to the inflated configuration, the scoring structure expands in a radially outward direction and remains in continuous compressive contact with at least a portion of the balloon as the balloon unfolds. The scoring structure also contracts in a radially inward direction and remains in continuous compressive contact with at least a portion of the balloon as the balloon deflates to the first diameter, thereby assisting in deflation of the balloon.

The scoring structure may be entirely free of attachment to the balloon and the catheter. In one embodiment, the scoring structure may extend at least substantially an entire length of the active portion. In another embodiment, the scoring structure may extend only partially along the length of the active portion. The scoring structure may include a plurality of longitudinal members connecting circumferentially compressible members, the longitudinal members and the circumferentially compressible members having an atraumatic radially inner surface in compressive contact with the balloon, and a radially outer surface shaped to engage and score a vessel wall when the balloon is expanded to the inflated configuration.

The foregoing paragraphs have been provided by way of general introduction, and are not intended to limit the scope of the following claims. The presently embodiments described below, will be best understood by reference to the following detailed description taken in conjunction with the accompanying drawings.

BRIEF DESCRIPTION OF THE DRAWINGS

The embodiments may be more fully understood by reading the following description in conjunction with the drawings, in which:

FIG. 2 is a side elevation view of the distal end of the scoring balloon catheter in an expanded configuration;

FIG. 3 is a cross-sectional view of the balloon and scoring structure of FIG. 2 along the line X'-X' in the expanded configuration;

FIG. 4 is a cross-sectional view of the balloon and scoring structure of FIG. 1(a) along the line X'-X' in the collapsed configuration;

FIGS. 5(a)-(g) illustrate various embodiments of the cross-sectional profile of the scoring structure;

FIGS. 13-15 illustrate the dilation of a body lumen using the scoring balloon catheter of FIG. 1(a), wherein FIG. 13 is a side view of the scoring balloon catheter of FIG. 1(a) in a collapsed configuration prior to dilation of a body lumen;

FIG. 14 is a side view of the scoring balloon catheter of FIG. 13 in the expanded configuration dilating the body lumen;

FIG. 15 is a side view of the scoring balloon catheter of FIG. 13 in a collapsed state after dilation of the body lumen;

DETAILED DESCRIPTION

Figure 1A:
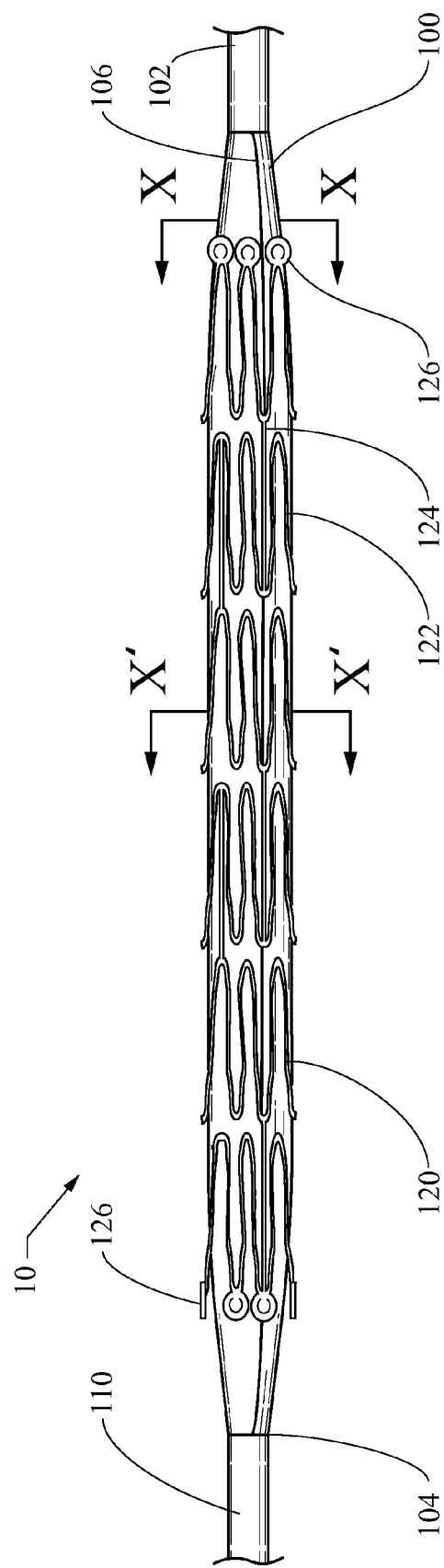
FIG. 1(a) is a side elevation view of a distal end of an embodiment of a scoring balloon catheter in a collapsed configuration.

Referring now to the figures, FIGS. 1(a)-(f) illustrate an embodiment of a scoring balloon catheter 10 for scoring a calcified/fibrous lesion and dilating a body lumen (e.g. a vessel or duct). As shown in FIG. 1(a) and (b), an embodiment of the scoring balloon catheter 10 may include a dilation balloon 100, a scoring structure 120, a catheter 110, and a hub 20 (FIG. 1(b)).

Figure 1B:
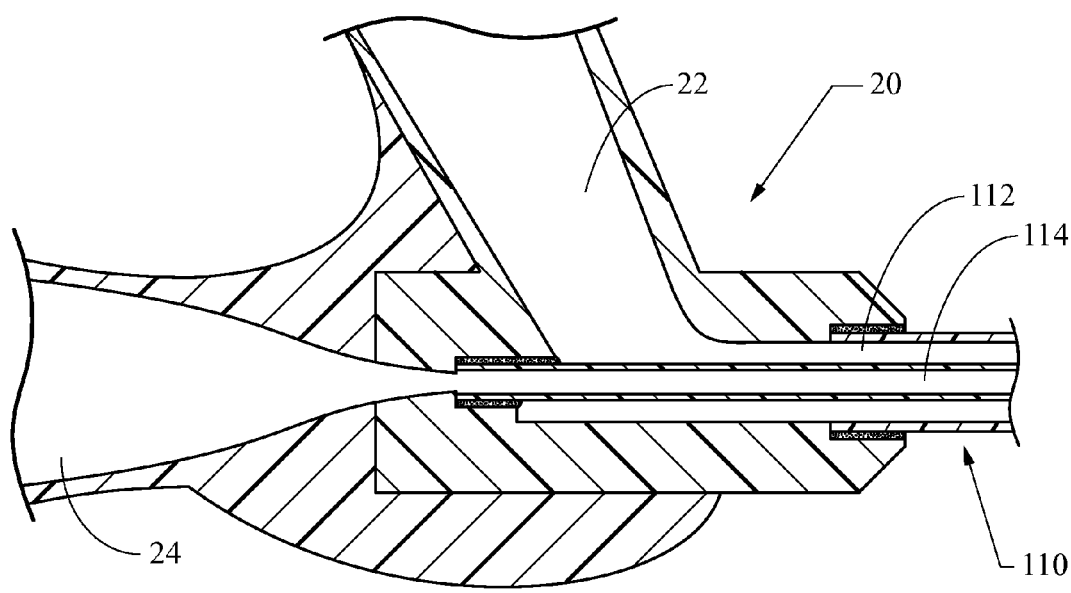
FIG. 1(b) is a side cross-sectional view of a hub of the scoring balloon catheter of FIG. 1(a).
Figure 1D:
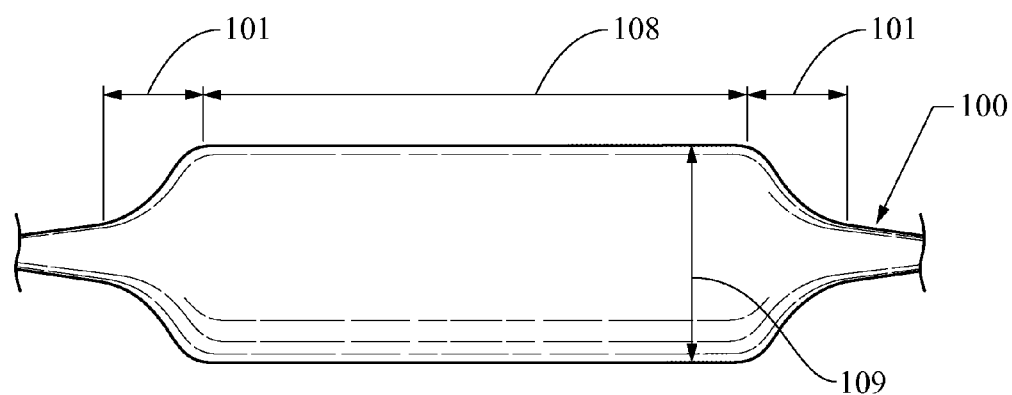
FIG. 1(d) is a side elevation view of the balloon of the scoring balloon catheter of FIG. 1(a) in an inflated state.

As shown in FIG. 1(d), the dilation balloon 100 may have proximal and distal tapered portions 101 that extend from the proximal and distal ends of a working region 108 to the proximal and distal ends of the dilation balloon 102, 104, respectively. In its inflated state, the working region 108 has a generally cylindrical, constant radius shape, and a length that is sized to substantially correspond to a length of the portion of a body lumen (e.g. a stenosis or lesion) to be dilated. For example, in one embodiment, the working region 108 may have a length ranging between about 20 mm to about 120 mm, and between about 20 mm and 40 mm in another embodiment.

The dilation balloon 100 may be sized to expand stenoses/lesions in the aorta, iliac, renal, coronary, popliteal, and carotid arteries, which typically have diameters ranging between about 2.0 mm and about 40 mm. Accordingly, the scoring balloon catheter 10 may range in size from 6 French or smaller up to approximately 15 French or larger.

Figure 1C:
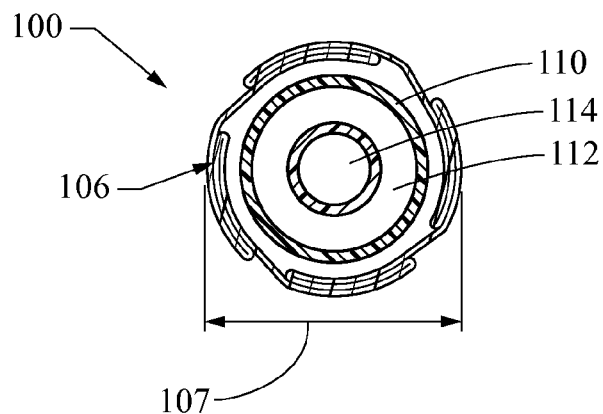
FIG. 1(c) is a cross-sectional view of a balloon of the scoring balloon catheter in a deflated state along the line X-X of FIG. 1(a)

The dilation balloon 100 is configured to be expandable between a deflated and folded configuration having a diameter 107 (FIG. 1(c)), to an inflated configuration having a diameter 109 (FIG. 1(d)). Because the purpose of the dilation balloon is to engage and expand a constricted body lumen, the inflated diameter of the dilation balloon 100 substantially matches the expected healthy diameter of the body lumen, which may be determined using the diameters of healthy unconstricted vessels disposed near or at one or both sides of the constriction. Accordingly, in one embodiment, the inflated diameter 109 of the dilation balloon 100 also ranges between about 2.0 mm and about 40 mm.

Because the dilation balloon 100 is specifically designed to expand strictures in a body lumen, the dilation balloon 100 may be made of a material having sufficient strength to prevent puncture or tearing when expanded against the sharp protrusions of a calcified lesion. Additionally, in order to avoid over expansion and rupturing of the blood vessel, the dilation balloon 100 may be constructed of materials that maintain their original shape when inflated to 8-20, or to greater than 20 atmospheres of pressure. Thus, the dilation balloon 100 may be made from a material that is substantially inelastic within the working pressure range of 14-20 atmospheres. For example, the balloon 100 may be made from polyethylene terephthalate (PET) or Nylon.

Furthermore, the scoring balloon catheter 10 may be used in body lumens having diameters of approximately 2.0 mm or less. In one embodiment, the balloon wall may be as thin as possible to minimize the folded, deflated diameter of the balloon 107. The smaller the body lumen, the smaller the package size. Thus, the dilation balloon 100 may be made of a material that is strong enough to withstand dilation pressures using a very thin wall. Exemplary dilation balloons, such as the Cook Accent Balloon Angioplasty Catheter, ATB PTA Dilatation Catheter, and Advance Low-Profile Balloon Dilatation Catheter balloon, made by Cook Incorporated, the assignee of the present application, are typically made from nylon or PET having a wall thickness of 0.0038 mm.

As shown in FIGS. 1(c) and (f), in the deflated state, the dilation balloon 100 forms a plurality of folds 106 to achieve a minimal diameter 107 for delivery of the scoring balloon catheter 10 to a treatment site in a patient's vasculature, e.g. a calcified or fibrous lesion. For example, the balloon 100 may be folded such that the folds 106 wrap around the catheter 110 in an overlapping configuration, as shown in FIG. 1(a). However, it should be understood that the present embodiment is not limited thereto, and the dilation balloon 100 may be folded in any configuration that results in a sufficiently small deflated diameter 107 for insertion into a body lumen. The dilation balloon 100 is hermetically sealed to the catheter 110 at the proximal and distal ends 102, 104.

The catheter 110 includes at least two lumens, an inflation lumen 112 in fluid communication with the interior space defined by the inner surface of the dilation balloon 100, and a guidewire lumen 114 adapted to receive a guidewire and allow contrast fluid or the like to be delivered to the treatment site. The inflation lumen 112 and the guidewire lumen 114 may be formed by two catheter tubes arranged in a substantially coaxial configuration, as shown in FIGS. 1(b) and (c). Alternatively, the inflation lumen 112 and the guidewire lumen 114 may be integrally formed in a single catheter tube.

As shown in FIG. 1(b), the inflation lumen 112 is connected to an inflation port 22 on the hub 20 and extends to at least the proximal end 104 of the balloon 100. The guidewire lumen 114 is connected to a guidewire port 24, and extends distally through an entire length of the balloon 100 to at least the distal end 102 such that the guidewire lumen 114 passes through, but is not in fluid communication with, the interior space of the dilation balloon 100. However, it should be understood that the present embodiment is not limited thereto, and other guidewire and inflation lumen 112, 114 configurations are contemplated, including, but not limited to rapid exchange configurations.

Figure 1E:
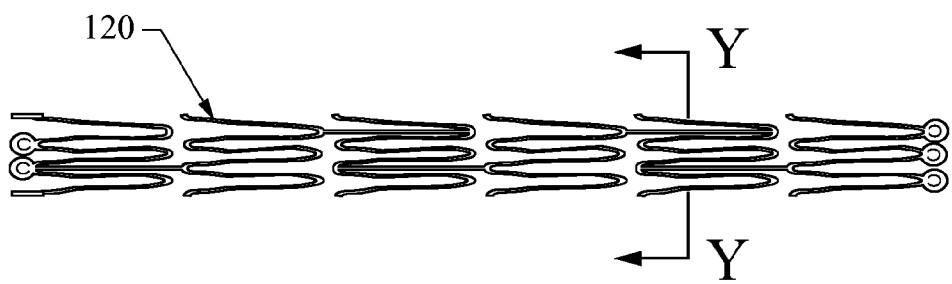
FIG. 1(e) is a side elevation view of the scoring structure of the scoring balloon catheter of FIG. 1(a) in an initial relaxed configuration.
Figure 1F:
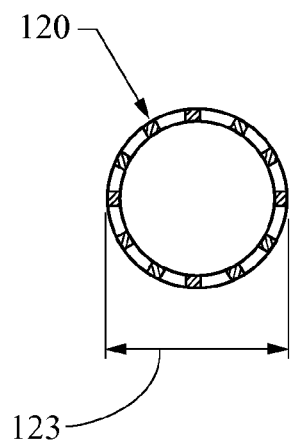
FIG. 1(f) is a cross-sectional view of the scoring structure of FIG. 1(e) along the line Y-Y.

As shown in FIGS. 1, 1(e), and 1(f), the scoring structure 120 is completely free of attachment to the dilation balloon 100 and the catheter 110. The scoring structure 120 may be formed of a plurality of structural members 122 connected by bends in an undulating pattern, and appears much like a balloon or self-expanding stent. However, unlike a self-expanding stent which has a fully expanded relaxed configuration, the scoring structure 120 has a relaxed configuration in which the diameter is reduced. Furthermore, because the scoring structure's 120 relaxed position is at its reduced diameter, it differs from a balloon expandable stent in that upon being expanded by the dilation balloon 100, the scoring structure 120 returns to its relaxed, reduced diameter state, as described below in detail. Thus, the scoring structure 120 expands and contracts with the inflation and deflation of the balloon 100 and is not capable of being implanted to support a body lumen. Stated differently, the scoring structure 120 is not capable of acting as a stent.

In a one embodiment, the structural members 122 are connected in an undulating pattern to form ring structures 125 having a substantially cylindrical shape. Each of the ring structures 125 are connected by longitudinal connecting members 124, resulting in a substantially continuous scoring structure 120 that extends substantially the entire length and circumference of the working region 108. The scoring structure 120 may also include radiopaque markers 126 disposed at the proximal and distal ends of the scoring structure 120 to allow for fluoroscopic visualization and placement of the scoring balloon catheter 10 within a body lumen. The radiopaque markers may be made of gold, tungsten, or platinum, or the like, as is known in the art, and may be formed as rivets attached to the scoring structure 120. Alternatively, portions of the proximal and distal ends of the scoring structure 120 may be coated with a radiopaque material.

The scoring structure 120 may be made of an elastic material or a super-elastic material. For example, the scoring structure 120 may be made from stainless steel or Nitinol, which allow the scoring structure 120 to expand and contract with the dilation balloon 100 without plastically deforming as the dilation balloon 100 is inflated to its maximum diameter 109, as shown in FIGS. 1(d) and 2, and deflated, as shown in FIGS. 1(a) and (c). Because the scoring structure 120 has a reduced diameter 123 that is less than the minimum diameter 107 of the dilation balloon 100, the scoring structure 120 continuously applies a compressive, radially inward force against the dilation balloon 100 in its deflated, inflated, and intermediate states. This compressive force exerted by the scoring structure 120 on the dilation balloon 100 may result in frictional force between the scoring structure 120 and the balloon 100 that prevents unwanted or unintended migration or displacement of the scoring structure 120 relative to the working region 108 during manufacturing and use. As a result, the need for physical attachment of the scoring structure 120 to the dilation balloon 100 may be obviated. In other embodiments, the scoring structure may be attached to the dilation balloon 100, the catheter 110, or other portions of the balloon catheter 10 by a wire, suture, or other means known in the art.

Because the scoring structure 120 is free of attachment to the dilation balloon 100 and the catheter 110, it offers significant manufacturing and operational advantages over conventional scoring balloons. For example, conventional scoring balloons employing metallic cutting members attached to the surface of a dilation balloon must be carefully folded to avoid contact between the sharp outer edge of the cutting member and the balloon to prevent the cutting member from lacerating or otherwise damaging the balloon during both manufacturing and inflation. Additionally, attaching the cutting members to the balloon in such catheters is difficult because the metal cutting members and the polymer balloon are dissimilar materials. In contrast, the scoring balloon catheter 10 of the present embodiment requires no specialized folding techniques or machinery and can be folded in substantially the same manner as a conventional angioplasty balloon catheter. Additionally, because the scoring structure 120 utilizes the compressive force to maintain its position relative to the dilation balloon 100, the scoring structure 120 requires no adhesive or crimping processes to place the scoring structure 120 on the dilation balloon 100, thereby dramatically simplifying the manufacturing process.

As shown in FIG. 1(a), in the initial relaxed position, circumferentially adjacent structural members 122 are substantially parallel to each other. However, as shown in FIG. 2, when the dilation balloon 100 is inflated, the radially outward force exerted on the scoring structure 120 by the dilation balloon 100 causes the substantially parallel structural members 122 to flex away from each other, thereby increasing the diameter of the scoring structure 120 and allowing the dilation balloon 100 to expand. As the dilation balloon 100 expands, the folds 106 begin to unfold and slide along the inner surface of the scoring structure 120 until the dilation balloon achieves its maximum inflated diameter 109, as shown in FIGS. 3-4.

When the dilation balloon 100 is deflated, the radially inward compressive force exerted by the scoring structure 120 assists in the deflation process and ensures that the scoring structure 120 remains in contact with the outermost portion of the surface of the dilation balloon 100. As the balloon 100 continues to deflate, the scoring structure 120 forces the balloon to fold in on itself until the compressive force exerted by the scoring structure 120 cannot compress the balloon any further. At this point, the dilation balloon 100 achieves a relaxed state approximating the minimum diameter 107.

The scoring structure 120 may be formed using the same processes known in the art to form stents, for example and without limitation, cannula or sheet cutting, and braiding. In the case of cannula and sheet cutting a desired arrangement of structural and longitudinal connecting members 124, 122 is cut into a metallic cannula or sheet using a laser or the like. This process typically results in relatively sharp edges along the cutting lines and may produce small, sharp protrusions along the edges of the structural and longitudinal connecting members 124, 122. In the case of the metallic sheet, once the desired geometry of the scoring structure 120 is cut, the sheet is rolled into a cylindrical form and welded or soldered together to form a tube, as is known in the art.

Figure 9:
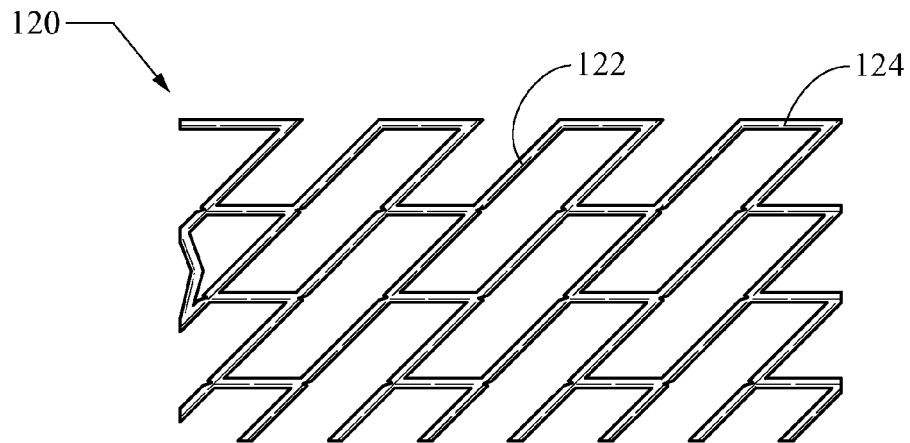
Figure 10:
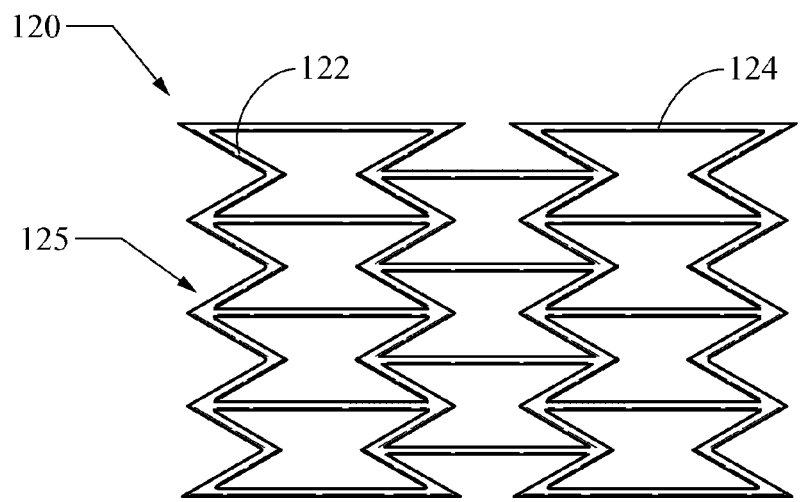
Figure 11:
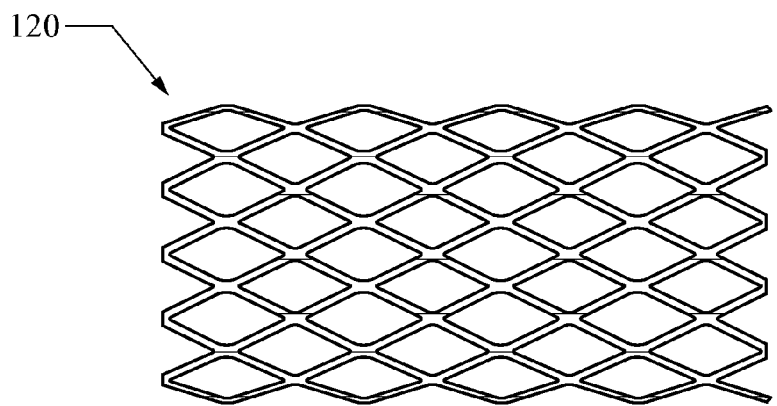
Figure 12A:
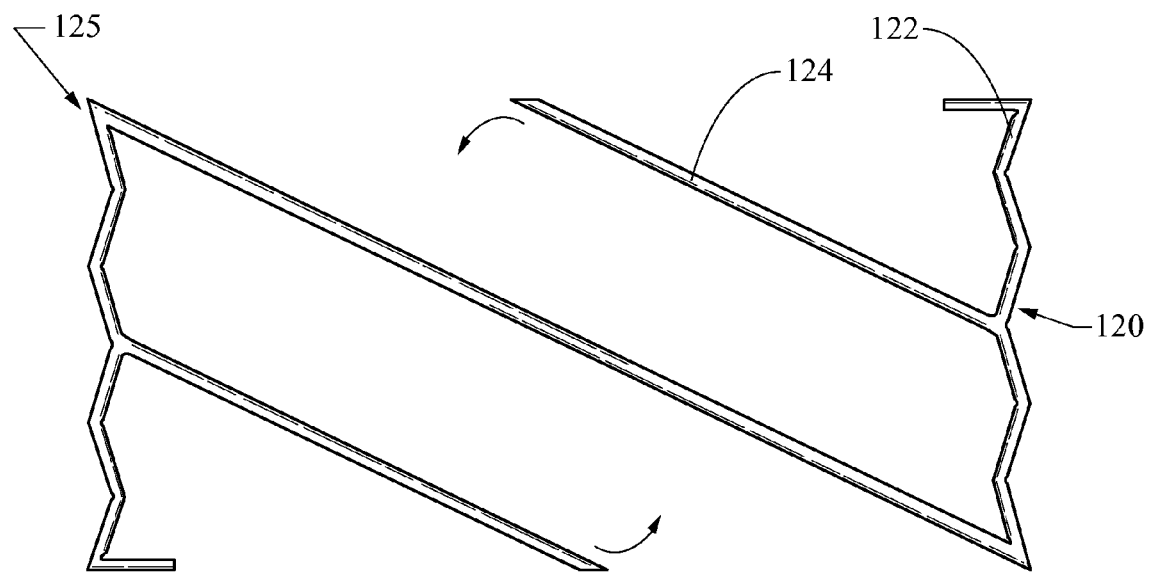
Figure 12B:
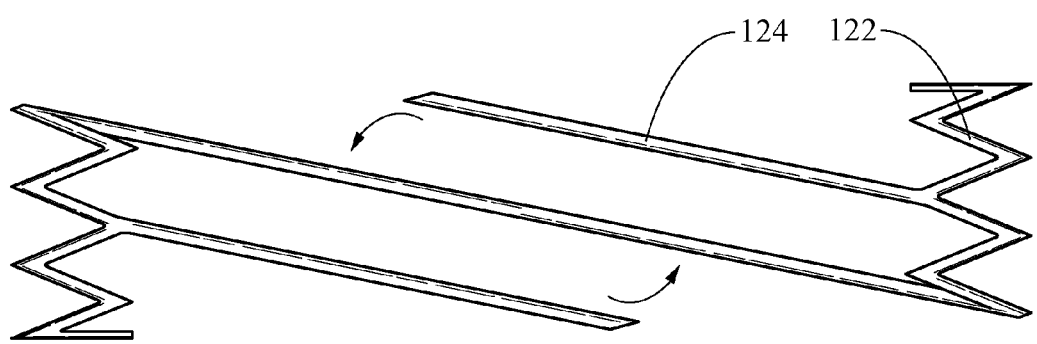

FIGS. 7-10, and 12 illustrate several exemplary embodiments of a cannula or sheet cut scoring structure 120, while FIG. 11 illustrates a scoring structure 120 formed by braiding or otherwise attaching a plurality of wire filaments together. FIGS. 7(a) and (b) illustrate a scoring structure 120 in an expanded and initial form, respectively. As shown in FIGS. 7(a) and (b), the scoring structure 120 has four ring structures 125 formed of interconnected structural members 122 that are connected by a plurality of longitudinal connecting members 124 to produce a scoring pattern having plurality of longitudinally staggered, substantially straight-lines for engaging a calcified or fibrous lesion. FIGS. 8(a) and (b) illustrate a scoring structure 120 having two ring structures 125 disposed at opposite ends thereof. The ring structures 125 are connected by substantially straight longitudinal connecting members 124. As shown in FIGS. 8(a) and (b), the longitudinal connecting members 124 extend substantially the entire length of the scoring structure 120, and therefore extend substantially the entire length of the working region 108 of the dilation balloon 100, thereby producing a substantially straight line scoring pattern. Similarly, in another embodiment, the longitudinal connecting members 124 may extend along the length of the scoring structure 120 in a helical or otherwise non-straight line pattern (FIGS. 12(a) and (b). FIGS. 9 and 10 illustrate additional embodiments having a substantially helically extending scoring pattern, and a zigzag pattern, respectively.

Turning to FIG. 5, the scoring structure 120 may have an outer surface that is shaped to engage and score a lesion or stenosis, and an atraumatic inner surface to prevent the scoring structure from damaging or rupturing the dilation balloon 100. FIGS. 5(a)-(d) illustrate several exemplary integrally formed cross-sectional shapes of the structural members 122 and longitudinal connecting members 124 of the scoring structure 120. In the embodiment shown in FIG. 5(a), the scoring structure 120 includes scoring portions 524a disposed at opposite corners on the radially outer surface of the scoring structure 120, and an atraumatic portion 522a disposed on the radially inner surface of the scoring structure 120. The scoring portions 524a are jagged protrusions, which may be formed as a by-product of the manufacturing process of the scoring structure 120 due to the cannula or sheet cut process described above. In this embodiment, the scoring structure 120 is used "as cut," thereby leaving the sharp protruding portions to act as scoring portions 524a. The atraumatic portions 522(a) and (c) may be formed by polishing or otherwise abrading the inner surface of the scoring structure 120 to remove sharp edges that could potentially scar or damage the dilation balloon 100.

FIG. 5(c) illustrates a cross-section in which the scoring portion 524c of the outer surface of the scoring structure 120 includes sharp edged corners. FIGS. 5(b) and (d) illustrate cross-sections that taper from broad atraumatic surfaces 522(b) and 522(d) disposed at an inner surface of the scoring structure 120 to pointed scoring portions 524(b) and 524(d). The pointed scoring portions 524(b) and 524(d) and the atraumatic portions 522(b) and 522(d) may be formed by chemical or mechanical etching, or machining for embodiments cut from cannula or sheet. In embodiments of the scoring structure 120 formed by braiding a plurality of wire filaments, the wire filaments may be extruded in the cross-sectional shapes illustrated in FIGS. 5(b) and (d).

FIGS. 5(e)-(g) illustrate cross-sectional views of scoring structures 120 having a composite shape in which a scoring member 540(e)-(g) having a stress concentrating scoring portion 524(e)-(g) is attached to a base portion 550(e)-(g) having an atraumatic inner surface 522(e)-(g). The scoring members 540(e)-(g) may be attached to the base portions 550(e)-(g) by bonding, welding, soldering or the like, as is known in the art. The scoring members 540(e)-(g) may be attached to an entire exterior surface of the scoring structure 120. Alternatively, the scoring members 540(e)-(g) may be applied to only selected portions of the scoring structure 120 to achieve a desired scoring pattern.

In another embodiment shown in FIGS. 16(a)-(d), the scoring structure 120 may have a circumferentially asymmetric scoring portion 1510 configured to score and dilate lesions extending only partially around an inner surface of a vessel or duct. In one embodiment, the asymmetric scoring structure 1500 may be formed by cutting two different, fluoroscopically (or otherwise visible from outside the patient) distinguishable geometric patterns of structural members 124 and longitudinal connecting members 122 in a cannula or sheet with a laser, water jet or the like. In this embodiment, the first geometric pattern corresponds to a scoring section 1510 and the second geometric pattern corresponds to an atraumatic section 1520. The first geometric pattern may correspond to a first portion of the scoring structure 120 that extends partially around the circumference, while the second geometric pattern may correspond to a second portion of the scoring structure extending around the remainder of the circumference. Accordingly, the first and second geometric patterns result in a circumferentially asymmetrical structure that is visually distinguishable in a manner clearly correlated to device orientation using fluoroscopy or the like.

Both the internal and external surfaces of the scoring structure 1500 having the second geometric pattern corresponding to the atraumatic portion 1520 are abraded through electro-polishing or the like, or coated with a layer of material, for example and without limitation, a radiopaque material such as gold, tungsten or platinum, to remove any sharp edges or protrusions that may damage healthy vessel tissue. Meanwhile, at least the external portion of the scoring structure 1500 having the first geometric pattern corresponding to the scoring portion 1510 is left in the "as-cut" state and/or formed with stress concentrating features 524 as described above in connection with FIGS. 5(a)-(g).

The "as cut" configuration of the portion of the scoring portion 1510 may be maintained by masking the portions of the scoring structure corresponding to the scoring portion 1510 prior to performing the surface finishing operation, e.g. electro-polishing or the like, which removes the sharp, "as cut" stress concentrating features 524 from the unmasked, atraumatic portion 1520. The masking protects the stress concentrating features 524 during the surface finishing operation such that when the masking is removed, the stress concentrating features 524 remain. In contrast, the unmasked, atraumatic portion 1520 is exposed to the surface finishing process and is therefore substantially free of stress concentrating features 524. Because nickel-titanium alloys such as Nitinol and stainless steel alloys are generally at least partially radiolucent, all, or portions of the scoring section 1510 and the atraumatic section 1520 may be modified for fluoroscopic visualization and differentiation from each other. For example, in embodiments where the atraumatic portion 522 is not covered by a radiopaque material, radiopaque markers may be attached to the scoring structure 120 at selected points to allow for fluoroscopic differentiation of the two geometric patterns, thereby allowing a physician to determine the orientation of the scoring portion 524 relative to the atraumatic portion 522. In another embodiment, the entire scoring structure 120 may be doped with a radiopaque material to allow fluoroscopic distinction of the two geometric patterns. However, it should be understood that the asymmetric scoring structure 1500 is not limited thereto, and other combinations and placement of radiopaque material on the scoring section 1510 and the atraumatic section 1520 are contemplated. Further, while FIGS. 16(*a*)-(*d*) illustrate the scoring section 1510 and the atraumatic section 1520 as having a particular geometric pattern of structural members 122 and longitudinal connecting members 124, the geometric patterns are not limited thereto, and any two patterns that are distinguishable from one another under fluoroscopic visualization are contemplated.

Figure 18A:
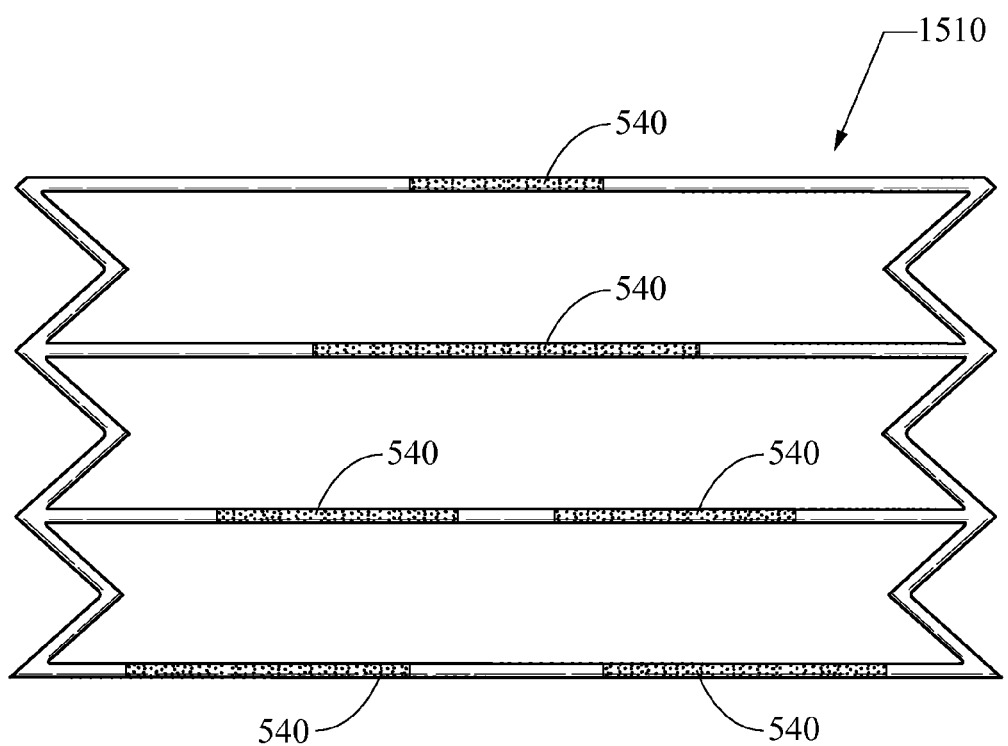
FIGS. 18(a) and (b) illustrate another embodiment of the asymmetrical scoring structure of FIGS. 16(a)-(d).
Figure 18B:
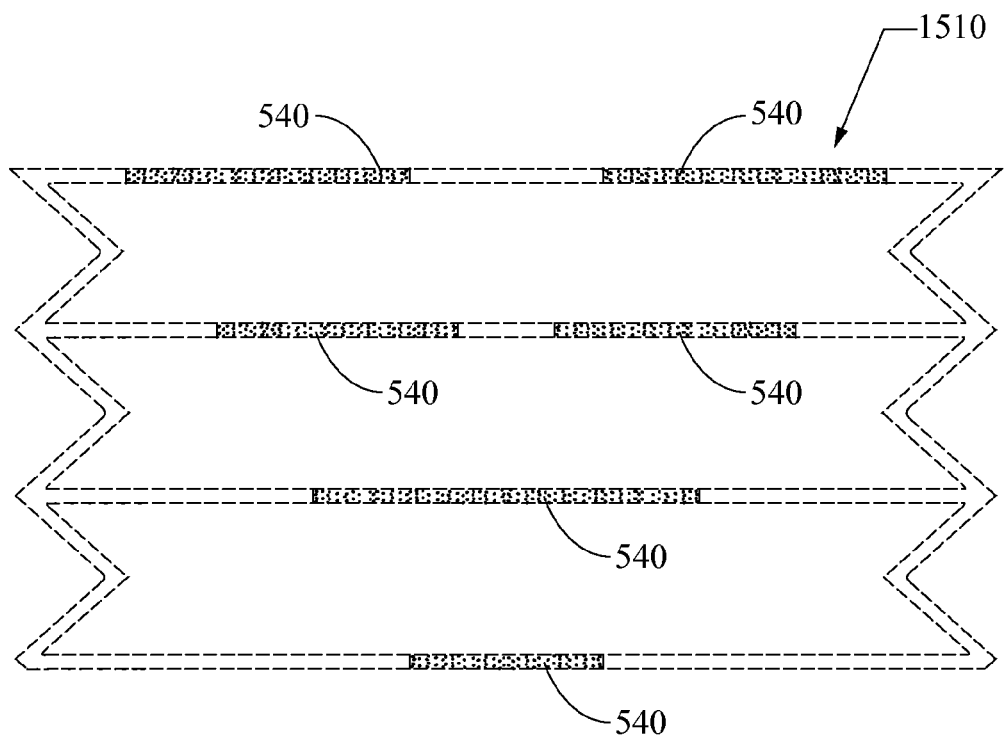

In an alternative embodiment, the entire scoring structure 120 may have the same or a different geometric pattern of structural members 122 and longitudinal members 124, and a scoring member 540 made of a radiopaque material may be attached to only a portion of the scoring structure 120. As shown in FIGS. 18(*a*) and (*b*), a plurality of scoring members 540 may be attached to the asymmetrical scoring structure 1500 in a pattern having, for example, a "V" shape that points in one direction or another, depending on which side the scoring structure 1500 is viewed. That is, when the asymmetric scoring structure 1500 is oriented such that the scoring section 1510 is disposed closest to the fluoroscopic imaging device (e.g. FIG. 18(*a*)), the scoring members 540 create an upwardly pointing V-shaped pattern. Conversely, when the asymmetric scoring structure 1500 is oriented such that the scoring section 1510 is disposed farthest away from the fluoroscopic imaging device (e.g. FIG. 18(*b*), the scoring members 540 create a downwardly pointing V-shaped pattern. Accordingly, depending on the direction the V-shaped pattern is pointing, the physician can ascertain the orientation of the scoring section 1510 and the atraumatic section 1520 and can align the scoring section 1510 with portion of the vessel covered by the lesion to be scored.

In another embodiment shown in FIGS. 16(*e*) and (*f*), the atraumatic section 1520 may include an orientation/identification indicator 1600 that allows the physician to identify the orientation of the scoring section 1510 and the atraumatic section 1520 under fluoroscopy. As shown in FIG. 16(*e*), when the asymmetric scoring structure 1500 is viewed in an orientation where the atraumatic section 1520 is disposed closest to the fluoroscopic imaging device, the asymmetrically extending shape of the orientation/identification indicator 1600, in this case a "V" shaped portion of a longitudinal member 124, appears to point upward. However, when the asymmetric scoring structure 1500 is viewed in an orientation where the atraumatic section 1520 is disposed farthest from the fluoroscopic imaging device, the orientation/identification indicator 1600 appears to point downward. Thus, depending on the orientation of the V-shaped orientation/identification indicator 1600 (e.g. upward vs. downward, leftward vs. rightward, etc.), the physician is able to determine where the atraumatic portion 1520 and the scoring portion 1510 are located in the vessel relative to the lesion. The physician can then manipulate the scoring balloon by rotation or the like to align the scoring section 1510 with portion of the vessel covered by the lesion to be scored. While FIGS. 16(*e*) and (*f*) illustrate the orientation/identification indicator(s) 1600 being disposed on the atraumatic section 1520, it should be understood that the orientation/identification indicator(s) may be disposed on the scoring portion 1510.

In some embodiments, the asymmetric scoring structure 1500 may include a plurality of orientation/identification indicators 1600 that indicate precisely which structural members 122 and longitudinal members 124 comprise the scoring and/or atraumatic sections 1510, 1520. In one embodiment, the orientation/identification indicators 1600 are included on at least the structural members 122 and longitudinal members 124 that define the border/edge of the atraumatic section 1520 or the scoring section 1510 and at least one intermediate structural member 122 or longitudinal member 124 thereof to aid the physician in determining which section of the asymmetric scoring structure 1500 that he/she is viewing and its orientation. Further, while the orientation/identification indicators 1600 are shown as pointing upward or downward in FIGS. 16(*e*) and (*f*), it should be understood that they are not limited thereto, and the orientation/identification indicators 1600 may be oriented in any direction that allows for identification and differentiation when viewed through fluoroscopy or the like.

Figure 17A:
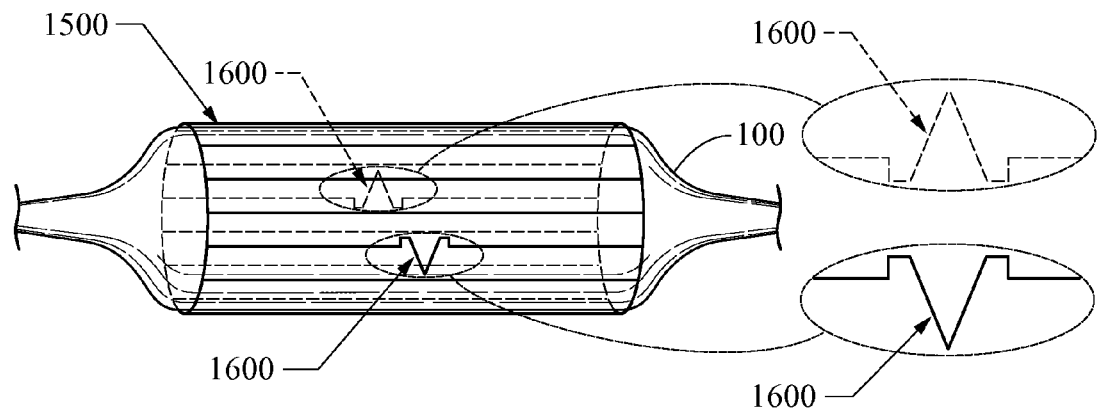
FIGS. 17 (a)-(c) illustrate different embodiments of the orientation/identification indicator of the embodiment of FIGS. 16(e) and (f)
Figure 17B:
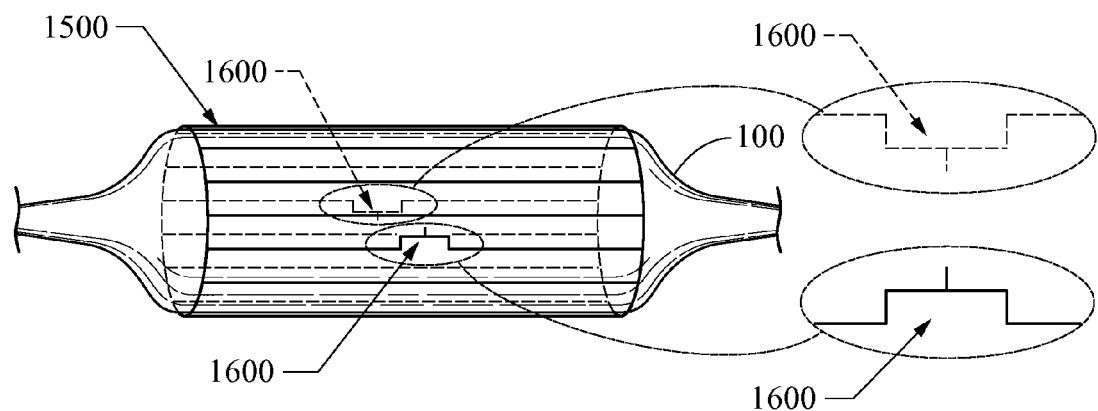
Figure 17C:
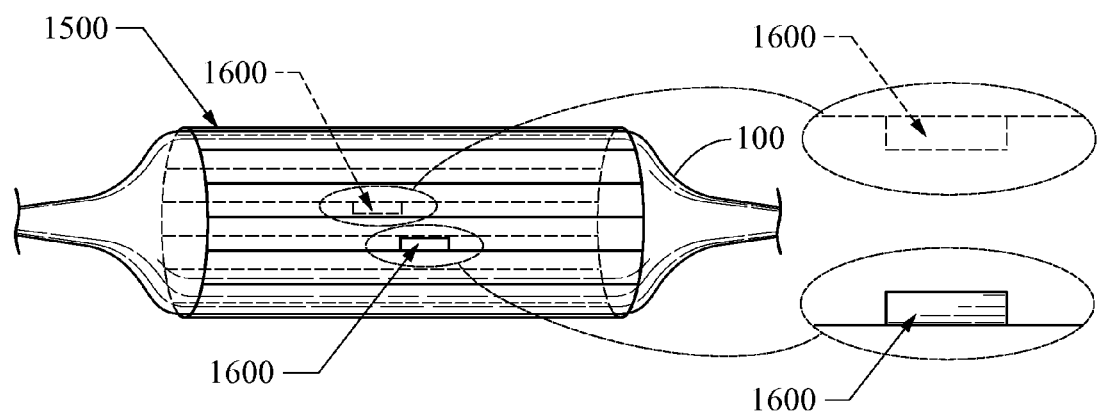

Moreover, as shown in FIGS. 17(*a*)-(*c*), the orientation/identification indicator 1600 is not limited to a "V" shape shown in FIGS. 16(*e*) and (*f*). The orientation/identification indicator 1600 may have any shape that results in a distinctly different orientation that is readily apparent when viewed from one side or the other of the asymmetric scoring structure 1500 through fluoroscopy or the like. Thus, the shape of the orientation/identification indicator 1600 may be, for example and without limitation, V-shaped, U-shaped, C-shaped, D-shaped, quadrilateral, oval, or the like. The orientation/identification indicator 1600 may be a solid tab that is integrally formed with or attached to a longitudinal member 124 or a structural member 122, as shown in FIG. 17(*c*). The orientation/identification indicator 1600 may also be a longitudinal/structural member 124, 122 having a particular shape, as shown in FIGS. 16(*e*) and (*f*) and 17(*a*) and (*b*).

Figure 6A:
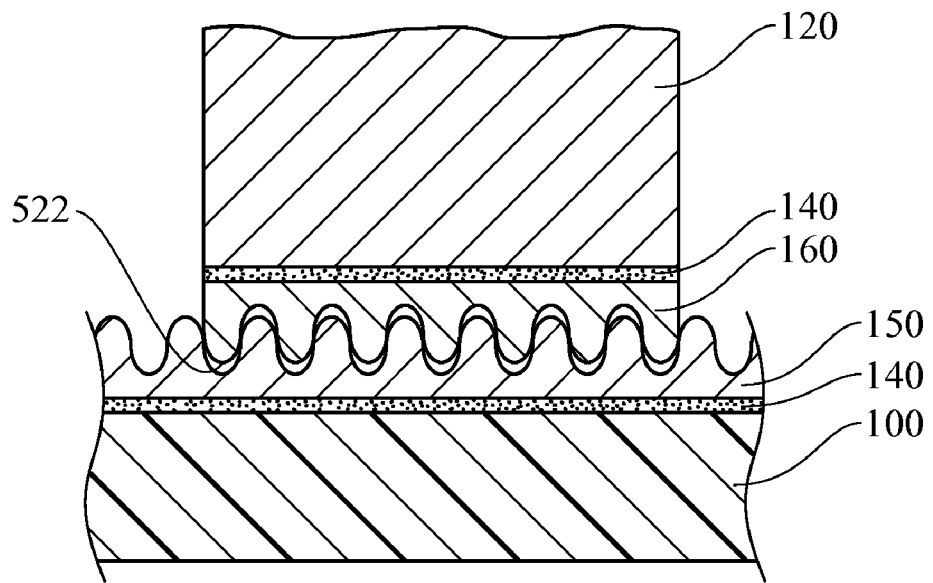
FIGS. 6(a) and (b) are close-up views of an interface between the balloon and the scoring structure.
Figure 6B:
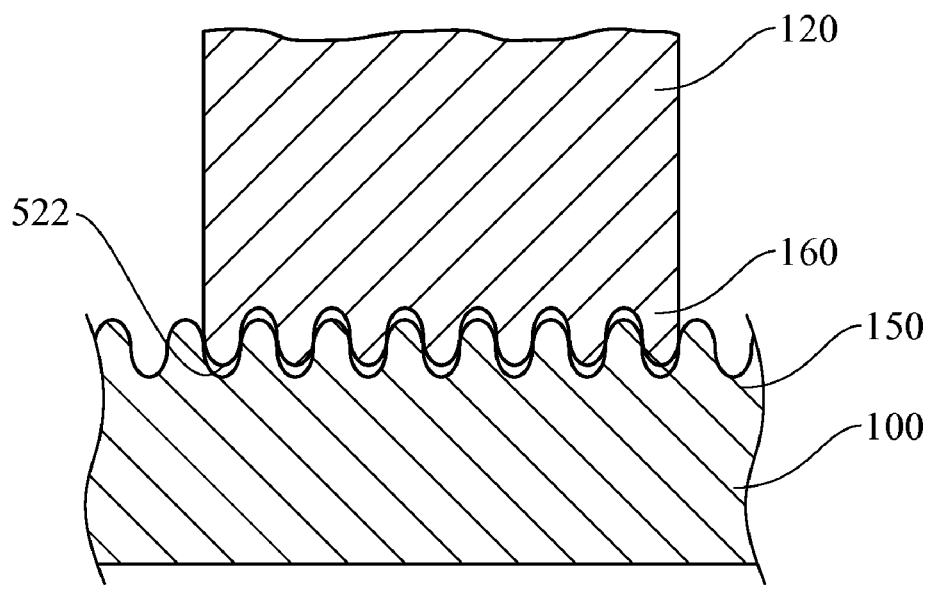
Figure 7A:
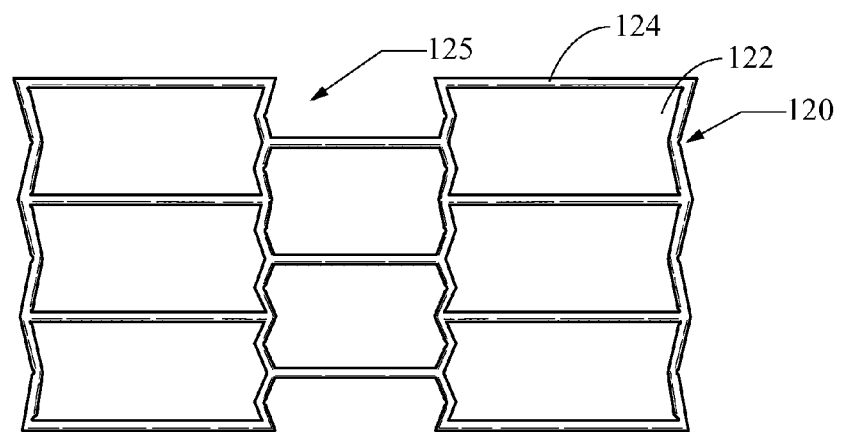
FIGS. 7(a)-12(b) illustrate a plurality of exemplary scoring structures.
Figure 7B:
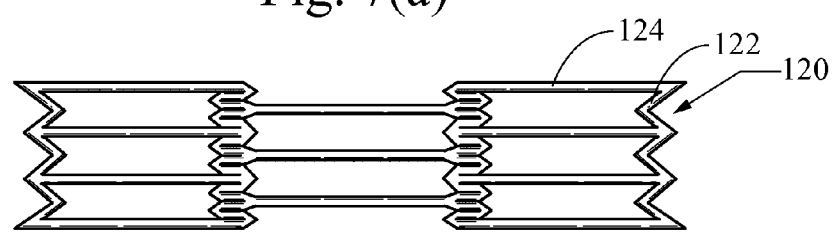
Figure 8A:
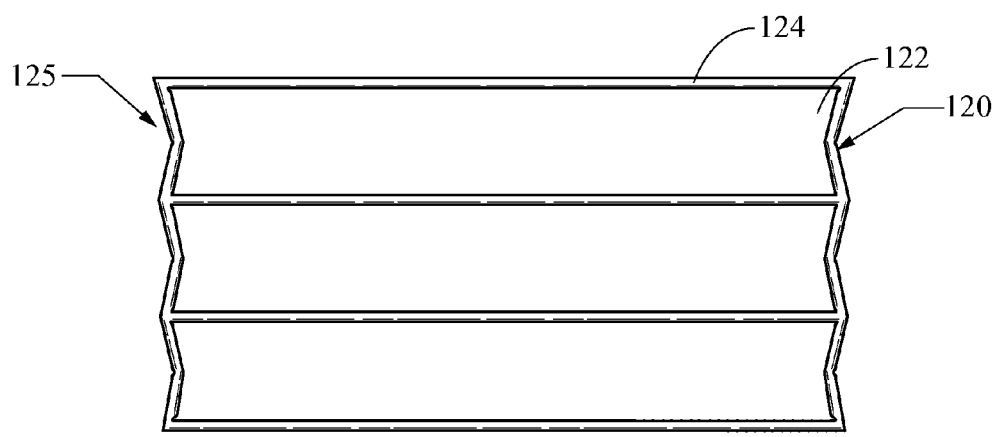
Figure 8B:
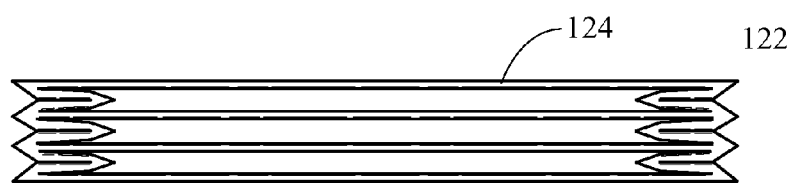

Turning to FIGS. 6(*a*) and (*b*), the outer surface of the dilation balloon 100 may have a first structure 150 and the atraumatic inner surface 522 of the scoring member 120 may have a second structure 160. As shown in FIG. 6(*a*), the first and second structures 150, 160 may be formed by applying a separate material to the surface of the dilation balloon 100 and the scoring structure 120 with an adhesive 140 or the like. Alternatively, as shown in FIG. 6 (*b*), the first and second structures 150, 160 may be integrally formed in the surface of the dilation balloon 100 and the scoring structure 120. The first and second structures 150, 160 are shaped to frictionally engaging each other thereby maintaining a longitudinal position of the scoring structure 120 relative to the dilation balloon 100 as the scoring structure 120 expands due to the expansion of the dilation balloon 100. For example, the first and second structures 150, 160 may be a series of grooves and protrusions having a complimentary shape that extends around a circumference of the dilation balloon 100 and the scoring structure 120, respectively. However, it should be understood that the structures 150, 160 are not limited thereto, and may have any shape capable of frictionally interacting to help maintain the longitudinal position of the scoring structure 120 relative to the dilation balloon 100.

In operation, the scoring balloon catheter 10 is inserted percutaneously (or via cutdown) into a patient's vasculature over a guidewire using the Seldinger technique, which is well known in the art. Initially, the guidewire is inserted through a small incision, typically made in a patient's groin, arm, or other anatomic location. The guidewire is then advanced through the patient's vasculature to the location of the stenosis or lesion 300 (the treatment site). Once the guidewire has passed the lesion 300 in the vessel 200, a distal tip of the guidewire is placed distally of the lesion 300. At this point, the guidewire is inserted into the distal end of the guidewire lumen outside the patient's body and the scoring balloon catheter 20 is advanced along the guidewire to the treatment site. A guide catheter may also be inserted into the patient's vasculature prior to insertion of the scoring balloon catheter 10, thereby providing a protective barrier between the scoring portion 124 and the vessel. The scoring balloon catheter 10 is then advanced along a track formed by the guidewire (or along a track formed by the guidewire and through the guide catheter) into the vessel and to the lesion 300 utilizing the radiopaque markers on the scoring structure or the balloon catheter, which are visible under fluoroscopy. In the event the lesion 300 only extends around a portion of the circumference of the vessel 200, the asymmetric scoring structure 1500 may be employed. In this case, the physician utilizes the fluoroscopically distinguishable patterns to "clock" the scoring structure 120 such that the scoring portion 124 is circumferentially aligned with the lesion 300 by rotating the proximal end of the scoring balloon catheter 10.

Figure 13:
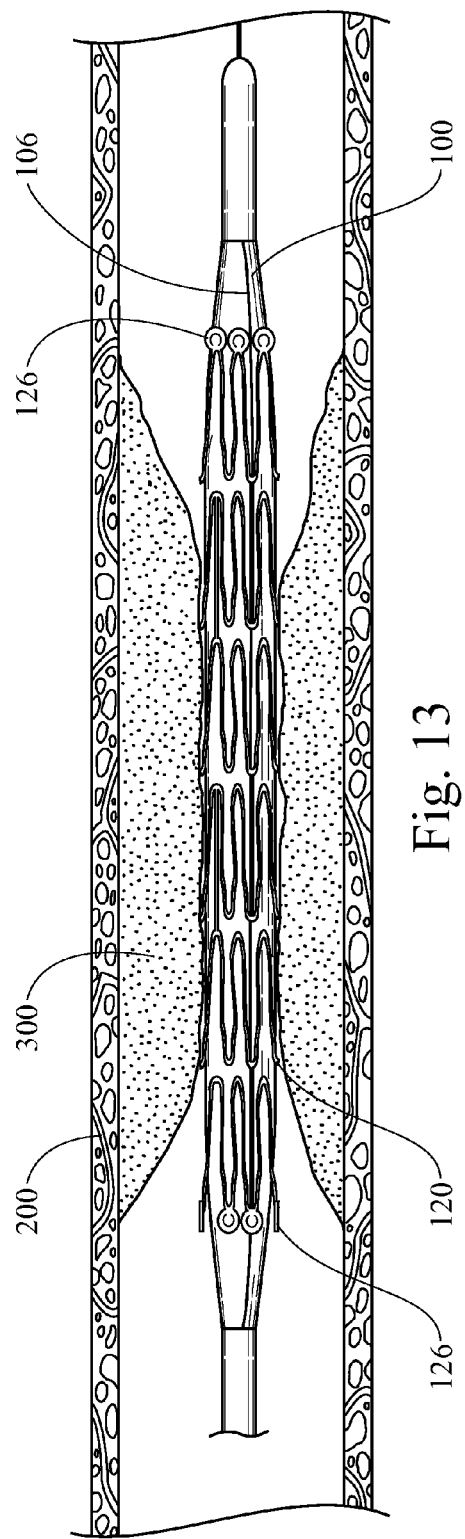
Figure 14:
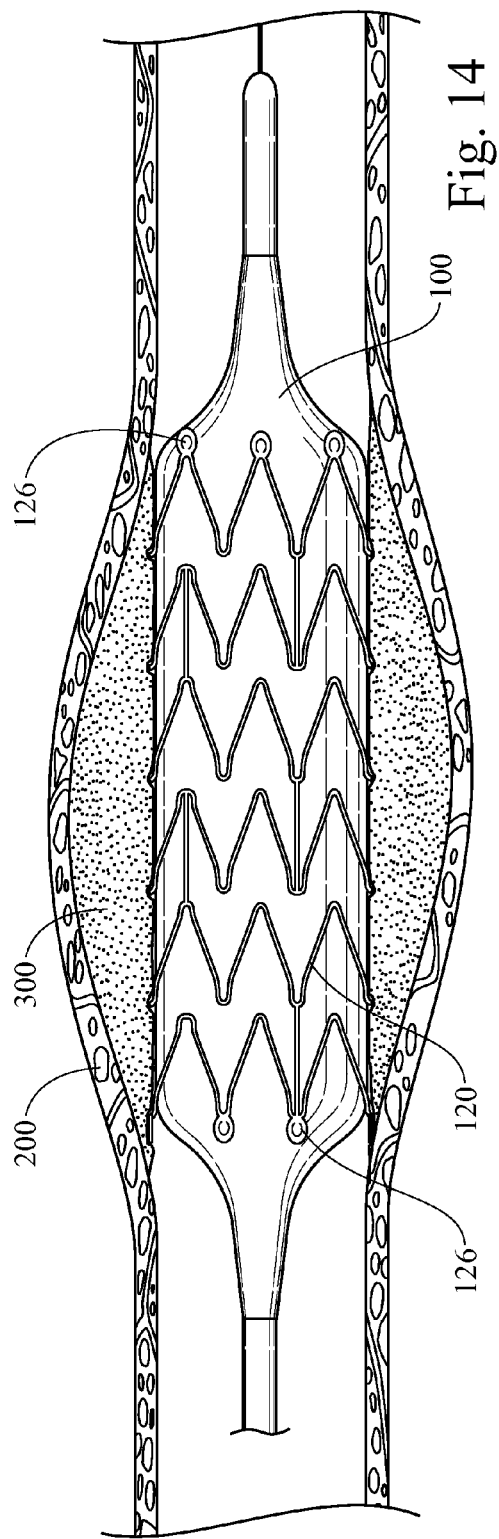

Once the scoring balloon catheter 10 has been advanced to a position just proximal of the lesion 300, the physician advances the scoring balloon catheter 10 out of the guide catheter to expose the scoring structure 120 and the balloon 100, as shown in FIG. 13. Next, as shown in FIG. 14, the dilation balloon 100 is inflated with a fluid, typically saline solution or a mixture of saline and contrast fluid, which causes the balloon 100 to expand and unfold, thereby expanding the scoring structure 120. As the balloon 100 continues to expand, the scoring structure 120 is forced against the lesion 300, which presses the scoring portion(s) 124 of the scoring structure 120 into the surface of the lesion 300. Because the scoring portion(s) 124 create stress concentrations at the points/corners, the scoring structure 120 concentrates the outward radial force exerted by the dilation balloon 100 at discreet areas, which allows the scoring structure 120 to fracture and/or compress the outer surface of the calcified or fibrous lesion, thereby scoring its surface. By scoring the lesion 300, the dilation balloon 100 can more easily and controllably dilate the portion of the vessel 200 corresponding to the lesion 300 utilizing a lower inflation pressure, as compared to an unscored lesion 300.

Additionally, in embodiments in which the scoring structure 120 is free from attachment to the dilation balloon 100, the scoring structure 120 may be less likely to dislodge particles of plaque from the lesion 300 if the scoring balloon catheter 10 is inadvertently jostled or rotated once the scoring structure 120 has engaged the lesion 300, thereby preventing potential complications from such dislodged plaque particles. Further, in embodiments where the scoring structure 120 is not attached to the dilation balloon 100, the scoring structure 120 may be better able to flex and adapt to the shape of the expanding dilation balloon 100 than in embodiments where the scoring structure 120 is attached to the dilation balloon 100, thereby helping to ensure that the scoring portion 124 is positioned to most fully engage the lesion 300.

Figure 15:
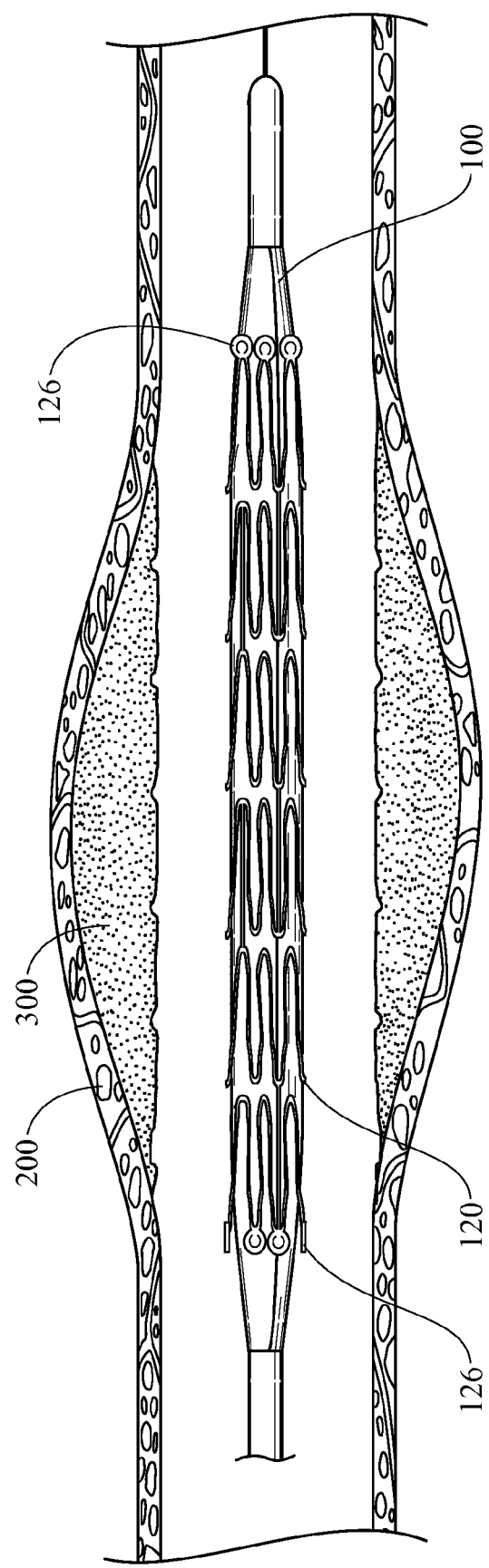
Figure 16A:
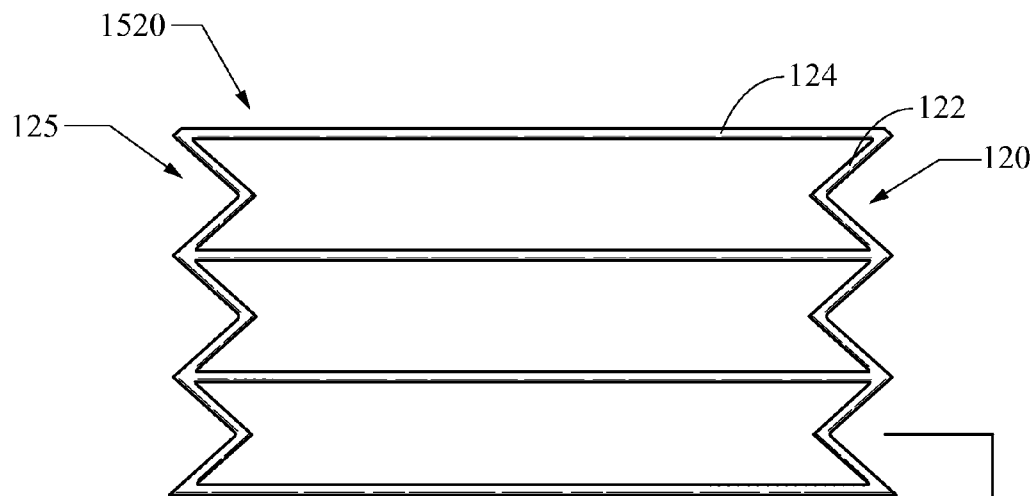
FIG. 16(a) is a side elevation view of a first portion of a circumferentially asymmetric embodiment of the scoring structure.
Figure 16B:
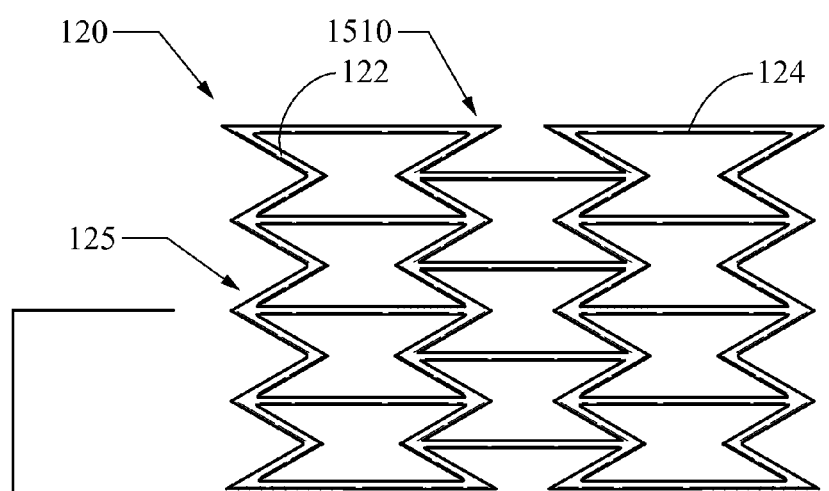
FIG. 16(b) is a side elevation view of a second portion of the asymmetric scoring structure of FIG. 15(a)
Figure 16C:
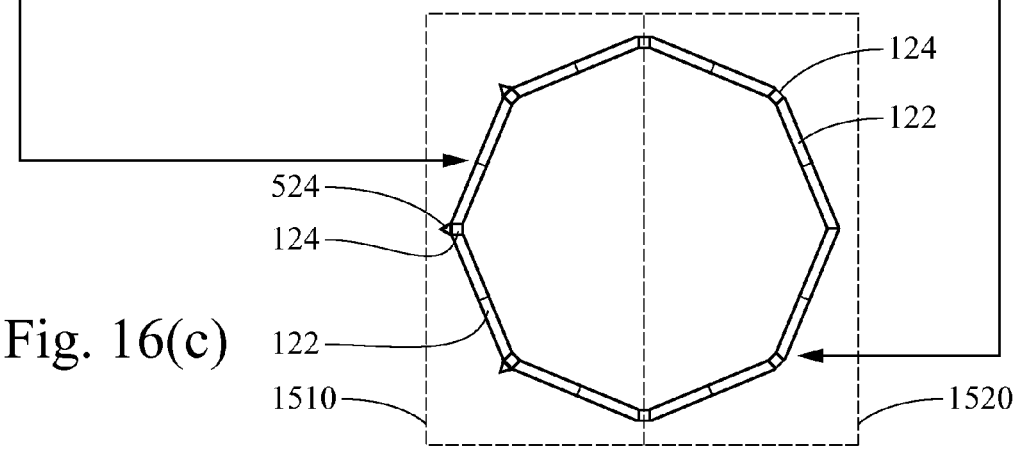
FIG. 16(c) is an end view of the asymmetric scoring structure.
Figure 16D:
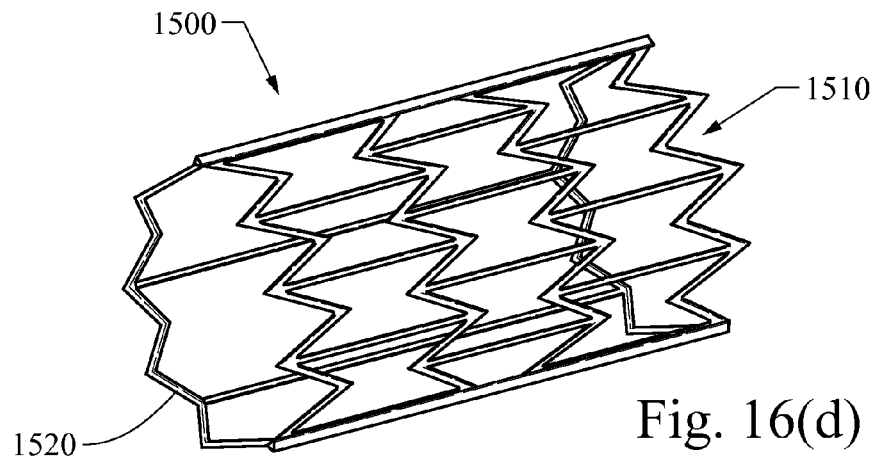
FIG. 16(d) is a perspective view of the asymmetric scoring structure.
Figure 16E:
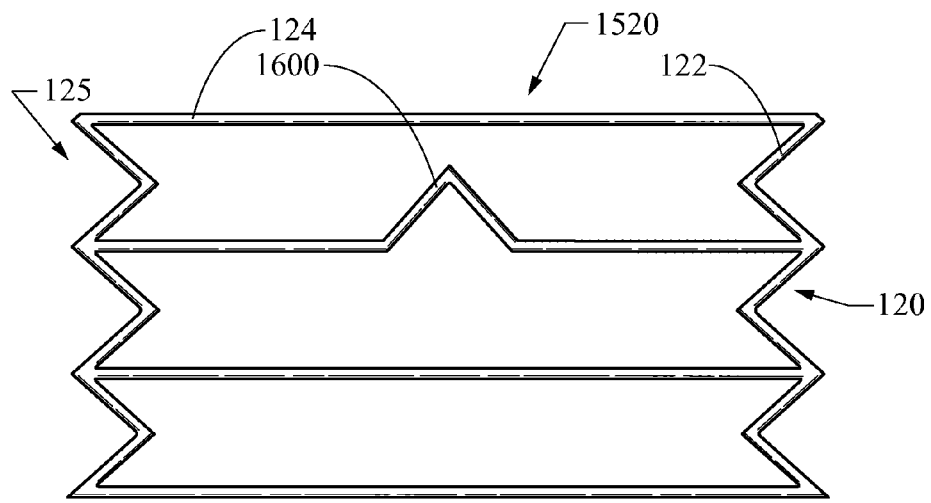
FIG. 16(e) is a side elevation view of a first side of an embodiment of the asymmetric scoring structure of FIGS. 16(a)-(e)
Figure 16F:
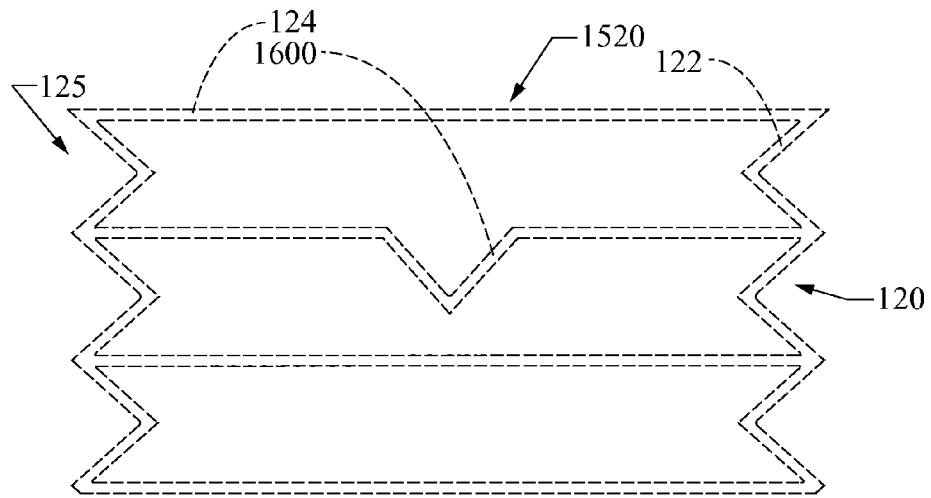
FIG. 16(f) is a side elevation view of a second side of the asymmetric scoring structure.

Once the vessel has been dilated, the dilation balloon 100 is then deflated and the scoring structure 120 contracts towards its relaxed diameter 127, as illustrated in FIG. 15. The scoring balloon catheter 10 is then withdrawn proximally and removed from the vessel.

While embodiments of the invention have been described above, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the features described above are not necessarily the only features of the invention, and it is not necessarily expected that all of the described features will be achieved with every embodiment of the invention.

The invention claimed is:

1. A balloon catheter for dilation of a vessel wall, comprising:
   a balloon having a distal portion, and a proximal portion, and a working region disposed therebetween, said working region being sized to dilate a vessel wall;
   a catheter having a distal end and a proximal end, said balloon being mounted on a distal portion of said catheter, wherein said catheter further comprises an inflation lumen extending therethrough in fluid communication with an interior region of said balloon, said balloon being expandable between a deflated configuration having a first diameter in which said balloon is folded and an inflated configuration having a second diameter in which said balloon is unfolded, said second diameter being greater than said first diameter;
   a circumferentially and longitudinally continuous metallic scoring structure having a diameter in an initial unrestrained relaxed state that is smaller than said first diameter of said balloon, wherein said scoring structure is disposed around an outer surface of said balloon in an expanded state, said scoring structure thereby continually exerting a radially inward compressive force against said balloon, such that when said balloon is expanded and contracted between said deflated configuration at said first diameter and said inflated configuration at said second diameter, said scoring structure expands and contracts in a radial direction and remains in continuous compressive contact with at least a radially outermost portion of said balloon as said balloon is inflated and deflated, said scoring structure returning toward its initial unrestrained relaxed state upon deflation of said balloon, said scoring structure thereby not being capable of being implanted to support said vessel wall;
   wherein said scoring structure is entirely free of attachment to said balloon and said catheter, said scoring structure comprising a plurality of structural members having an atraumatic radially inner surface in compressive contact with said balloon, and a radially outer surface shaped to engage and score a vessel wall when said balloon is expanded to said inflated configuration, said structural members of said scoring structure being connected in an undulating pattern forming a plurality of ring structures, each of said ring structures having a substantially cylindrical shape, and a plurality of longitudinal members extending between and connecting each of said ring structures in a continuous uninterrupted manner.

2. The balloon catheter of claim 1, wherein said scoring structure is formed of a super elastic material.

3. The balloon catheter of claim 2, wherein said super elastic material is nitinol.

4. The balloon catheter of claim 1, wherein said radially outer surface of said scoring structure has at least one point of stress concentration.

5. The balloon catheter of claim 1, wherein said radially outer surface of said scoring structure tapers from a first width to a second width, said first width being disposed radially inward of said second width, and wherein said first width is greater than said second width.

6. The balloon catheter of claim 1, wherein said longitudinal members extend along said outer surface of said balloon and parallel to a central axis thereof in both said inflated and deflated configurations.

7. The balloon catheter of claim 1, wherein said longitudinal members have a helical shape extending longitudinally and circumferentially along at least a portion of a length and a circumference of said balloon in said inflated configuration.

8. The balloon catheter of claim 1, wherein said scoring structure extends substantially an entire length of said working region.

9. The balloon catheter of claim 1, wherein said scoring structure is formed from a metallic cannula having super elastic and/or shape memory properties.

10. The balloon catheter of claim 1, wherein said outer surface of said balloon has a first structure and said atraumatic inner surface of said scoring member has a second structure, said first and second structures frictionally engaging each other, thereby maintaining a longitudinal position of said scoring structure relative to said balloon as said scoring structure expands due to said expansion of said balloon to said inflated configuration.

11. The balloon catheter of claim 10, wherein said first and second structures are a series of grooves and protrusions extending around a circumference of said balloon and said scoring structure, respectively.

12. A balloon catheter for dilation of a vessel wall, comprising:
a balloon having a distal portion, and a proximal portion, and a working region disposed therebetween, said working region being sized to dilate a vessel wall;
a catheter having a distal end and a proximal end, said balloon being mounted on a distal portion of said catheter, wherein said catheter further comprises an inflation lumen extending therethrough in fluid communication with an interior region of said balloon, said balloon being expandable between a deflated configuration having a first diameter in which said balloon is folded and an inflated configuration having a second diameter in which said balloon is unfolded, said second diameter being greater than said first diameter;
a circumferentially and longitudinally continuous metallic scoring structure having a diameter in an initial unrestrained relaxed state that is smaller than said first diameter of said balloon, said scoring structure extending substantially an entire length of said working region, wherein said scoring structure is disposed around an outer surface of said balloon in an expanded state, said scoring structure thereby continually exerting a radially inward compressive force against said balloon, such that when said balloon is expanded and contracted between said deflated configuration at said first diameter and said inflated configuration at said second diameter, said scoring structure expands and contracts in a radial direction and remains in continuous compressive contact with at least a radially outermost portion of said balloon as said balloon is inflated and deflated; said scoring structure returning toward its initial unrestrained relaxed state upon deflation of said balloon, said scoring structure thereby not being capable of being implanted to support said vessel wall;
wherein said scoring structure comprises a plurality of longitudinal members connecting circumferentially compressible members, each of said circumferentially compressible members comprising one of a plurality of ring structures, each ring structure forming an undulating pattern substantially cylindrical in shape, said longitudinal members and said circumferentially compressible members having an atraumatic radially inner surface in compressive contact with said balloon, and a radially outer surface having a scoring portion and an atraumatic portion, said scoring portion being shaped to engage and score a vessel wall when said balloon is expanded to said inflated configuration.

13. The balloon catheter of claim 12, wherein said atraumatic portion of said radially outer surface is fluoroscopically distinguishable from said scoring portion.

14. The balloon catheter of claim 12, wherein said circumferentially compressible members and longitudinal members of a first portion of said scoring structure corresponding to said atraumatic portion of said radially outer surface are arranged in a first pattern and said circumferentially compressible members and longitudinal members of a second portion of said scoring structure corresponding to said scoring portion of said radially outer surface are arranged in a second pattern, said second pattern being different and fluoroscopically distinguishable from said first pattern.

15. The balloon catheter of claim 12, wherein a first ring structure of said plurality of ring structures is disposed at a proximal end of said working region of said balloon and a second ring structure is disposed at a distal end of said working region of said balloon, and wherein said plurality of longitudinal members extend between and connect said first and second ring structures in a continuous uninterrupted manner.

16. A balloon catheter for dilation of a vessel wall, comprising:
a balloon having a distal portion, and a proximal portion, and a working region disposed therebetween, said working region sized to dilate a vessel wall;
a catheter having a distal end and a proximal end, said balloon being mounted on a distal portion of said catheter, wherein said catheter further comprises an inflation lumen extending therethrough in fluid communication with an interior region of said balloon, said balloon being expandable between a deflated configuration having a first diameter in which said balloon is folded and an inflated configuration having a second diameter in which said balloon is unfolded, said second diameter being greater than said first diameter;
a circumferentially and longitudinally continuous metallic scoring structure having a diameter in an initial unrestrained relaxed state that is smaller than said first diameter of said balloon, wherein said scoring structure is disposed around an outer surface of said balloon in an expanded state, said scoring structure thereby continually exerting a radially inward compressive force against said balloon, such that when said balloon is expanded and contracted between said deflated configuration at said first diameter and said inflated configuration at said second diameter, said scoring structure expands and contracts in a radial direction and remains in continuous compressive contact with at least a radially outermost portion of said balloon as said balloon is inflated and deflated, said scoring structure returning toward its initial unrestrained relaxed state upon deflation of said balloon, said scoring structure thereby not being capable of being implanted to support said vessel wall;

wherein said scoring structure is entirely free of attachment to said balloon and said catheter, said scoring structure extending only partially along a length of said working region, said scoring structure having a radially inner surface in compressive contact with said balloon, and a radially outer surface shaped to engage and score a vessel wall when said balloon is expanded to said inflated configuration, said scoring structure comprising a plurality of ring structures each forming an undulating pattern substantially cylindrical shape, and a plurality of longitudinal members extending between and connecting each of said ring structures in a continuous uninterrupted manner.

17. The balloon catheter of claim 16, wherein said scoring structure has at least one sharp outer edge, wherein said longitudinal members and said ring structures have an atraumatic radially inner surface in compressive contact with said balloon.

* * * * *